United States Patent [19]

Regnier et al.

[11] 4,312,869

[45] Jan. 26, 1982

[54] MONOSUBSTITUTED PIPERAZINES

[75] Inventors: Gilbert Regnier, Chatenay Malabry; Jacques Bure, Neuilly-sur-Seine, both of France

[73] Assignee: Science Union et Cie, Suresnes, France

[21] Appl. No.: 186,273

[22] Filed: Sep. 11, 1980

Related U.S. Application Data

[62] Division of Ser. No. 28,049, Apr. 9, 1979.

[30] Foreign Application Priority Data

Apr. 13, 1978 [GB] United Kingdom ............... 14565/78

[51] Int. Cl.³ .................. A61K 31/495; C07D 403/04
[52] U.S. Cl. .................................... 424/250; 544/367; 544/387; 544/388; 548/202; 548/203
[58] Field of Search ......................... 424/250; 544/367

[56] References Cited

U.S. PATENT DOCUMENTS 4,112,092 9/1978 Regnier et al. ..................... 544/367

Primary Examiner—Donald G. Daus
Assistant Examiner—James H. Turnipseed
Attorney, Agent, or Firm—Gordon W. Hueschen

[57] ABSTRACT

Biphenylalkylene-thiazolyl-piperazines of the formula

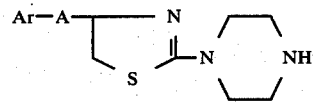

wherein Ar and A are as defined herein, e.g., 1-[4-(4-phenylsulfinylbenzyl)-2-thiazolyl]piperazine, and 1-[4-(4-biphenylylmethyl)-2-thiazolyl]piperazine, and their physiologically tolerable salts are provided. These compounds are useful as medicines for the treatment of inflammation with an immunological component, and are useful as hypolipemic and hypocholesterolemic agents and to assist lowering of lipid and cholesterol content in the blood.

12 Claims, No Drawings

MONOSUBSTITUTED PIPERAZINES

CROSS REFERENCES

This is a division of our application Ser. No. 028,049, filed Apr. 9, 1979.

SUMMARY OF THE INVENTION

Briefly, this invention provides new biphenylyl- and phenyl-X-phenylalkylene-thiazolyl-piperazines and their pharmacologically acceptable salts, which are used as medicines in the treatment of anti-inflammatory conditions associated with secondary immunitary reactions. These compounds are also useful in preventing the uptake in the blood of mammals, including valuable warm blooded animals, of lipids including triglycerides and cholesterol, and to assist in removing excess fatty substances from the blood.

DETAILED DESCRIPTION OF THE INVENTION

The present invention provides monosubstituted piperazines of the formula

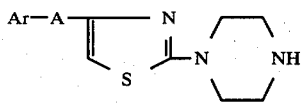
I in which: A is selected from the group consisting of —(CH$_2$)$_n$—, in which n is selected from 1, 2, and 3, and

in which R is selected from the group consisting of alkyl radicals having from 1 to 5 carbon atoms, inclusive, a trifluoromethyl radical, an unsubstituted phenyl radical and phenyl radicals mono- and polysubstituted by a substituent selected from the group consisting of halogen atoms, alkyl and alkoxy radicals each having from 1 to 5 carbon atoms, inclusive, and a trifluoromethyl radical, and Ar is a radical of the formula

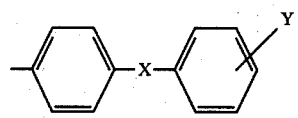

wherein:
X is selected from the group consisting of a single bond, an oxygen atom, a sulfur atom, a sulfinyl radical (SO), a sulfonyl radical (SO$_2$), and a carbonyl radical, and
Y is selected from the group consisting of a hydrogen atom, halogen atoms and alkyl and alkoxy radicals each having from 1 to 5 carbon atoms, inclusive.

In the definitions hereinabove, there may be mentioned, for example, as halogen atoms: chlorine, bromine, and fluorine atoms, as alkyl radicals: methyl, ethyl, propyl, butyl, and pentyl radicals and as alkoxy radicals: methoxy, ethoxy, propoxy, butoxy and pentyloxy radicals.

The present invention also provides acid addition salts of the compounds of the general formula I. The acid addition salts are preferably physiologically tolerable acid addition salts.

Among these compounds, there may be mentioned as particularly interesting the compounds of the formula I, wherein Ar is as defined above and A is —CH$_2$—, and their physiologically tolerable salts.

The present invention further provides a process for preparing a compound of the general formula I, which comprises condensing a halo compound of the general formula:

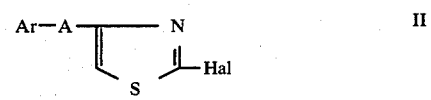
II in which Ar and A have the meanings given above and Hal represents a chlorine or a bromine atom, with an excess of piperazine.

Such a process is advantageously carried out by reacting the compound II with piperazine in solution in an aliphatic alcohol containing 4 or 5 carbon atoms, at a temperature within the range of from 110° to 140° C. The amount of piperazine may be from 2 to 5 times the stoicheiometric quantity, the excess acting as acceptor for the hydrogen halide formed during the reaction.

The present invention also provides a process for preparing a compound of the general formula I, which comprises condensing a halo compound of the general formula:

Ar-A-CO-CH$_2$-Hal    III in which Ar, A and Hal have the meanings given above, with a 1-substituted-4-thiocarbamoyl piperazine of the general formula

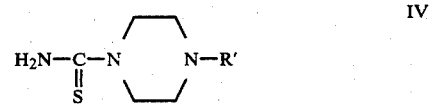
IV in which R' is a protecting group, for example, such as a formyl or an alkoxycarbonyl, preferably an ethoxycarbonyl radical, then hydrolyzing the resulting compound of the general formula:

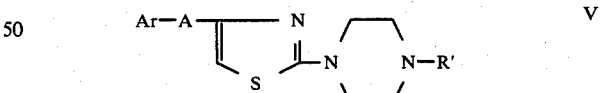
V in which Ar, A and R' have the meanings given above.

Such a process is advantageously carried out by reacting the compounds III and IV in solution in a polar solvent, for example, such as an aliphatic alcohol having from 2 to 4 carbon atoms, preferably at the boiling temperature of such a mixture, viz within the range of from 75° to 115° C., then hydrolyzing the protecting group with a strong base, for example, such as sodium or potassium hydroxide, in the same solvent.

The starting materials used for these processes are known compounds, or they may be prepared according to methods described in the literature for preparing similar compounds as mentioned in the following examples.

The compounds of the general formula I are strong bases which may be converted by treatment with acids into acid addition salts. As acids which may be used for the formation of these addition salts, there may be mentioned, for example, in the mineral series: hydrochloric, hydrobromic, sulphuric and phosphoric acids; and in the organic series: acetic, propionic, maleic, fumaric, tartaric, citric, oxalic, benzoic, methanesulfonic and 2-hydroxy ethane sulfonic acid ($CH_2OH-CH_2-SO_3H$).

The compounds of the formula I may be purified by physical methods, for example, crystallization or chromatography, or by chemical methods, for example, by formation of an addition salt followed by crystallization of the latter and decomposition thereof with an alkaline agent.

The compounds of the general formula I possess valuable pharmacological and therapeutic properties, especially antiinflammatory properties, mainly when they are in connection with the starting of a secondary immunitary reaction.

They may, therefore, be used as medicines, especially in the fields in which there are some inflammatory symptoms dependent on an action of lymphocytes, mainly in chronic inflammatory pathology with autoimmune etiology (nephritis, thyroiditis, etc.) or with an autoimmune component comprising rheumatoid diseases, collagenosis, Crohn's disease, etc.; in chronic infectious pathology, caused by parasites, bacteria, virus and slow virus, with an inflammatory component in ORL, respiratory, urogenital, central nervous system or digestive tract areas (glomerulonephritis, endocarditis, pancreatitis with insulitis, hepatitis, chronic bronchitis, etc.) as adjuvant to antiinfectious treatments or as independent treatment, and in some chronic and antiflammatory pathologies induced by other heteroantigens (transplant rejection, dermatitis by contact, and some chronic asthma, etc.).

The compounds of the general formula I and physiologically tolerable salts thereof also possess hypolipemic and hypocholesterolemic properties. They may, therefore, be used as medicines especially in the prevention and treatment of atheroma, lipid-metabolism disorders which may be either genetic disorders or dyslipemia secondary to glucids abnormalities, contraceptive pills, diabetes and obesity.

The toxicity of the compounds of this invention is low, as is evidenced by their having $LD_{50}$ values determined in mice to be greater than 2 g/kg perorally.

The activity of these new compounds on lipid-metabolism was evidenced in rats submitted to different diets.

These compounds were administered to rats receiving a lipid increased food for a period of four days at daily doses which may vary from 5 to 50 mg/kg P.O. according to the compounds.

The animals were killed two hours after the last administration. There was then observed a decrease of the plasma triglycerides level up to 80% by comparison with untreated animals.

Similarly, these compounds were administered to rats receiving a 2% cholesterol diet, for a period of four days at daily doses which may vary from 5 to 50 mg/kg P.O. according to the compounds.

The animals were killed two hours after the last administration, and there was then observed a decrease of the plasma cholesterol level up to 50%, by comparison with untreated animals.

The antiinflammatory activity was determined, among others, by the test of Siegmund, E. A., et. al., Proc. Soc. Exp. Biol. Med., (1957), 95, 729. When the compounds of the invention were administered to mice per orally at a dose of 50 mg/kg, there were observed inhibitions of the cramps provoked in the mice by the phenylbenzoquinone I.P. up to 93%.

The immunomodulating effect was studied according to the test of Asherson, et. al., Immunology (1968), 15, 405. When the compounds of the invention were administered to mice per orally at doses within the range of 25 to 100 mg/kg, there were observed inhibitions of the inflammation in connection with cutaneous hypersensibility induced in mice by oxazolone which may reach 77%.

The present invention also includes pharmaceutical compositions containing as active ingredient a compound of the general formula I or a physiologically tolerable acid addition salt thereof, in admixture or conjunction with a pharmaceutically suitable carrier, such, for example, as distilled water, glucose, lactose, starch, talc, ethyl cellulose, magnesium stearate or cocoa butter.

The pharmaceutical compositions of the present invention are advantageously in unit dosage form, and may contain from 20 to 200 mg of the active ingredient.

These pharmaceutical compositions may be (according to the desired therapeutical effect) in the form of tablets, dragees, capsules, liposomes for oral or injectable administration, suppositories, injectable or drinkable solutions, soluble preparations for intra-articular infiltrations, ointments, spray or aerosols, and may be administered by oral, rectal, parenteral or topical route at a dose of active ingredient within the range of 20 to 200 mg, one to four times a day.

The following examples illustrate the invention, the melting points being determined in a capillary tube, unless otherwise stated.

EXAMPLE 1

1-[4-(4-phenylsulfinylbenzyl)-2-thiazolyl] piperazine

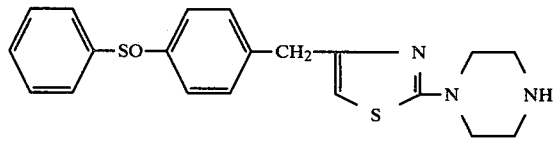

First Method

A solution of 6.4 g of 2-bromo-4-(4-phenylsulfinylbenzyl)thiazole (M. P. Kofler: 102° C.) and 6.5 g of anhydrous piperazine in 200 ml of butanol was refluxed for ten hours. Then, the solvent was evaporated and the thus obtained raw oil was taken off with 200 ml of a N solution of $CH_3SO_3H$. The insoluble matter was extracted twice with, each time, 20 ml of ether, then alkalized with $K_2CO_3$. The thus salted out oil was extracted twice with, each time, 50 ml of chloroform. The chloroform solution was washed with water, dried and evaporated. There was obtained 6.1 g of 1-[4-(4-phenylsulfinylbenzyl)-2-thiazolyl]piperazine, as semicrystallized product.

This product was taken off by ethanol and treated with a solution of HCl in ether in order to give 4.8 g of the corresponding dihydrochloride, in form of beige crystals melting (Kofler) at 158°–160° C.

The starting 2-bromo-4-(4-phenylsulfinylbenzyl)-thiazole was prepared by mild oxydation of 2-bromo-4-(4-phenylthiobenzyl)thiazole, M.P. 82° C., by the means of meta-chloroperbenzoic acid in chloroform.

Second Method

A solution of 14.6 g of 1-(4-phenylsulfinylphenyl)-3-chloroacetone and 8.7 g of 1-formyl-4-thiocarbamoyl piperazine, melting (Kofler) at 228° C., in 250 ml of ethanol at 90%, was boiled for one hour. There was added to the hot solution a solution of 9.3 g of KOH at 85% in 10 ml of water, and the mixture was refluxed for three hours, in order to hydrolyze the formyl protecting group. Then the solvent was evaporated off under reduced pressure, and the oily residue was taken up with 200 ml of a N hydrochloric acid solution. The insoluble matter was extracted with ether. The acid solution was alkalized with $K_2CO_3$, and the resulting base was extracted thrice with, each time, 50 ml of chloroform. The chloroform part was washed with water, then the solvent was evaporated off. There was obtained 16 g of 1-[4-(4-phenylsulfinylbenzyl)-2-thiazolyl]piperazine, as raw base, M.P. of its dihydrochloride: 158°-160° C.

The starting 1-(4-phenylsulfinylphenyl)-3-chloro acetone was prepared by mild oxydation in chloroform, of 1-(4-phenylthiophenyl)-3-chloro acetone with meta-chloro perbenzoic acid.

The starting 1-formyl-4-thiocarbamoyl piperazine was prepared in analogy to the method described by Conroy and Denton, J. Org. Chem. 18, 1489 (1953), starting from 4-formylpiperazine thiocyanate, M.P. 118° C.

EXAMPLE 2

1-[4-(4-phenylsulfonylbenzyl)-2-thiazolyl] piperazine

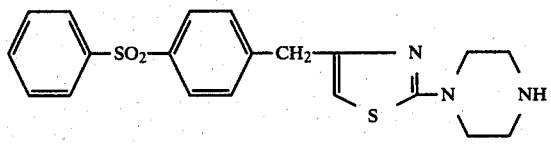

This product, the dihydrochloride of which melts (Kofler) at 170° C., was prepared:
according to the first method given in Example 1, starting from 2-bromo-4-(4-phenylsulfonylbenzyl)-thiazole, M.P. (Kofler): 165° C., and an excess of piperazine, and
according to the second method given in Example 1, starting from 1-(4-phenylsulfonylphenyl)-3-chloro-acetone and 1-formyl-4-thiocarbamoyl piperazine.

EXAMPLES 3 to 9

The following compounds were prepared in the manner described in the first method given in Example 1, starting from an appropriate 2-bromo (or chloro)-4-substituted thiazole and an excess of piperazine, and in the manner described in the second method given in Example 1, starting from an appropriate 1-substituted 3-chloro (or bromo) acetone and 1-formyl (or ethoxycarbonyl)-4-thiocarbamoyl piperazine.

3: 1-[4-(4-biphenylylmethyl)-2-thiazolyl] piperazine, M.P. of its dihydrochloride hemihydrate: 215°-220° C. (methanol/ether).
4: 1-[4-(4-phenoxybenzyl)-2-thiazolyl] piperazine, M.P. of its hydrochloride: 236°-242° C. (anhydrous methanol/ether).
5: 1-[4-(4-p. chlorophenoxybenzyl)-2-thiazolyl] piperazine, M.P. of its dihydrochloride: 195°-200° C. (anhydrous ethanol).
6: 1-[4-(4-phenylthiobenzyl)-2-thiazolyl] piperazine, M.P. of its hydrochloride: 165°-170° C. (anhydrous ethanol).
7: 1-[4-(4-benzoylbenzyl)-2-thiazolyl] piperazine, M.P. of its dihydrochloride hemihydrate: 230°-232° C. (methanol at 95%).
8: 1-[4-(4-p. chlorophenylthiobenzyl)-2-thiazolyl] piperazine.
9: 1-[4-(4-p. chlorobenzoylbenzyl)-2-thiazolyl] piperazine.

The following examples illustrate the pharmaceutical compositions containing as active ingredient a compound of the general formula I.

EXAMPLE 10

Formulation for one coated tablet containing 0.100 g of active ingredient:
1-[4-(4-phenylthiobenzyl)-2-thiazolyl] piperazine, hydrochloride: 0.100 g
lactose: 0.085 g
microcrystalline cellulose: 0.050 2 g
colloidal silica: 0.000 2 g
polyvinylpyrrolidone: 0.010 g
magnesium stearate: 0.0015 g
talc: 0.005 g coating glycerol: 0.000 35 g
hydroxypropylmethylcellulose: 0.006 35 g
sodium laurylsulfate: 0.000 04 g
titania: 0.001 9 g
polyoxyethylene glycol 6 000: 0.001 16 g
magnesium stearate: 0.000 2 g

EXAMPLE 11

Formulation for one capsule containing 0.100 g of active ingredient:
1-[4-(4-benzoylbenzyl)-2-thiazolyl] piperazine, dihydrochloride: 0.100 g
carboxymethyl starch: 0.005 g
microcrystalline cellulose: 0.087 8 g
colloidal silica: 0.000 2 g
magnesium stearate: 0.001 g
talc: 0.006 g
for one capsule n°1

We claim:
1. A compound selected from the group consisting of a monosubstituted piperazine of the formula

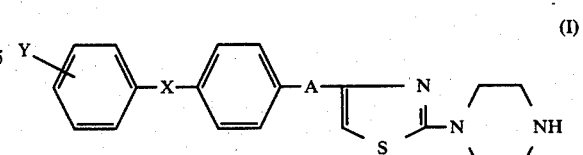

(I)

in which:
A is selected from the group consisting of —(CH$_2$)$_n$— in which n is selected from 1, 2, and 3, and

in which R is selected from the group consisting of alkyl having from 1 to 5 carbon atoms, inclusive, trifluoromethyl, unsubstituted phenyl and phenyl mono- and poly-substituted by a substituent selected from the group consisting of halogen, alkyl and alkoxy each having from 1 to 5 carbon atoms, inclusive, and trifluoromethyl, and X is selected from the group consisting of a single bond, oxygen, sulfur, sulfinyl, sulfonyl, and carbonyl, and Y is selected from the group consisting of hydrogen, halogen, and alkyl and alkoxy each having from 1 to 5 carbon atoms, inclusive, and physiologically tolerable acid addition salts thereof.

2. Compounds of claim 1 of the general formula

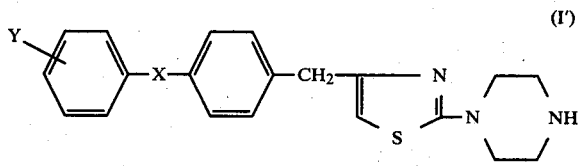

(I')

wherein X and Y have the meanings given in claim 1, and physiologically tolerable acid addition salts thereof.

3. A compound of claim 1, which is 1-[4-(4-biphenylyl-methyl)-2-thiazolyl] piperazine, and its dihydrochloride.

4. A compound of claim 1, which is 1-[4-(4-phenoxybenzyl)-2-thiazolyl] piperazine, and its hydrochloride.

5. A compound of claim 1, which is 1[4-(4-p-chlorophenoxybenzyl)-2-thiazolyl] piperazine, and its dihydrochloride.

6. A compound of claim 1, which is 1-[4-(4-phenylthiobenyzyl)-2-thiazolyl] piperazine, and its hydrochloride.

7. A compound of claim 1, which is 1-[4-(4-benzoylbenzyl)-2-thiazolyl] piperazine, and its dihydrochloride.

8. A compound of claim 1, which is 1-[4-(4-phenylsulfinylbenzyl)-2-thiazolyl] piperazine, and its dihydrochloride.

9. A compound of claim 1, which is 1-[4-(4-phenylsulfonylbenzyl)-2-thiazolyl] piperazine, and its dihydrochloride.

10. A pharmaceutical composition containing as active ingredient a compound of claim 1 in an amount of 20 to 200 mg, together with a suitable pharmaceutical carrier.

11. A method for treating a living animal body afflicted with inflammation having an immunological component, comprising the step of administering an amount of a compound of claim 1, which is effective for the alleviation of the said condition.

12. A method for the control of cholesterol and lipid blood content in a living animal, comprising the step of administering an amount of a compound of claim 1, which is effective for said purpose.

* * * * *